United States Patent
Pruett et al.

(10) Patent No.: US 7,197,405 B1
(45) Date of Patent: Mar. 27, 2007

(54) INTERACTIVE METHOD OF PROVIDING ANALYSIS OF POTENCY AND PURITY OF PHARMACEUTICAL COMPOUNDS

(75) Inventors: Earl Michael Pruett, St. Louis, MO (US); Russell D. Odegard, Eureka, MO (US)

(73) Assignee: Medpro Holdings, LLC, St. Louis, MO (US)

( * ) Notice: Subject to any disclaimer, the term of this patent is extended or adjusted under 35 U.S.C. 154(b) by 0 days.

(21) Appl. No.: 11/051,419

(22) Filed: Feb. 4, 2005

Related U.S. Application Data

(60) Provisional application No. 60/541,995, filed on Feb. 5, 2004.

(51) Int. Cl.
*G01N 31/00* (2006.01)

(52) U.S. Cl. ............... 702/30; 702/32; 250/339.12

(58) Field of Classification Search .......... 702/22, 702/27, 28, 30, 32, 127; 250/339.07, 371, 250/301, 339.12, 390.07; 356/51, 70, 239.6
See application file for complete search history.

(56) References Cited

U.S. PATENT DOCUMENTS

| | | | |
|---|---|---|---|
| 6,618,138 B2 | 9/2003 | Khoury | |
| 6,667,802 B2 | 12/2003 | Faus et al. | |
| 6,765,212 B2 | 7/2004 | Goetz et al. | |
| 6,771,369 B2* | 8/2004 | Rzasa et al. | 356/326 |
| 7,006,214 B2 | 2/2006 | Rzasa et al. | |
| 2002/0108892 A1 | 8/2002 | Goetz et al. | |
| 2003/0009385 A1* | 1/2003 | Tucciarone et al. | 705/26 |
| 2003/0128804 A1 | 7/2003 | Poteet et al. | |
| 2003/0168585 A1* | 9/2003 | Wall | 250/281 |
| 2004/0155202 A1 | 8/2004 | Poteet et al. | |
| 2005/0077476 A1 | 4/2005 | Poteet et al. | |
| 2005/0130881 A1* | 6/2005 | Shashoua | 514/8 |

* cited by examiner

*Primary Examiner*—Manuel L. Barbee
(74) *Attorney, Agent, or Firm*—Polster, Lieder, Woodruff, & Lucchesi, L.C.

(57) ABSTRACT

A computer facilitated, interactive method of requesting an spectrographic analysis of a sample having an unknown concentration or purity, performing an energy absorbance analysis of the sample to obtain spectrographic data regarding the analysis and comparing the spectrographic data to a stored spectrographic data regarding the analyses of the samples having a predetermined concentration and purity to determine the concentration or purity of the sample having an unknown concentration or purity. The requester can electronically request the analysis and monitor the progress of the analysis. The results of the analysis are electronically transmitted to the requester in real time.

35 Claims, 7 Drawing Sheets

INTERACTIVE METHOD OF PROVIDING ANALYSIS OF POTENCY AND PURITY OF PHARMACEUTICAL COMPOUNDS

CROSS-REFERENCE TO RELATED APPLICATIONS

This application claims the benefit of provisional patent application Ser. No. 60/541,995, filed Feb. 5, 2004, and which is incorporated herein by reference.

STATEMENT REGARDING FEDERALLY SPONSORED RESEARCH OR DEVELOPMENT

Not applicable.

BACKGROUND OF THE INVENTION

This invention relates to methods of conducting business comprising verifying the identity and determining the concentration, potency, purity and presence of contaminants, including, but not limited to, microbial, endotoxins and particulate matter in a mixture of ingredients, and a series of integrated systems and processes for the organization, monitoring and reporting of such analyses and related metadata through an electronic network.

Pharmacies generally compound pharmaceuticals that are not readily available on the market, for example, but not limited to, specialized dosage forms, certain oncological formulations, pediatric formulations, certain ophthalmic preparations, intravenous solutions, or other compounded pharmaceuticals referred to as compounded sterile preparations ("CSPs"). In the past, the pharmacists generally followed good compounding practices mandated by federal and state pharmacy practice acts and accepted professional compounding techniques. However, these CSPs have not been subject to concentration and purity guidelines set forth by the United States Food and Drug Administration ("FDA") or other regulatory bodies. If a compounding pharmacy wanted to analyze a product for potency or purity, it was required to engage outside testing laboratories that employed traditional analysis such as gas chromatography or other analytical procedures to test the individual CSPs. These processes are costly and time consuming and employed only on a limited basis.

It recently has been discovered that some pharmacies have failed to meet the concentration guidelines set forth by the prescribing physician, or have produced pharmaceuticals having high levels of impurities, microbial, endotoxin and particulate matter. In response, the regulatory bodies have set forth guidelines requiring that extemporaneous CSPs prepared under high-risk conditions be tested for concentration and purity prior to distribution to ensure the safety of the pharmaceutical for public use. Moreover, it is anticipated that in the future, regulatory bodies will set forth compounding guidelines for all CSPs, regardless of risk.

While the guidelines set forth by the regulatory bodies have resulted in safer and more reliable CSPs, the testing of each batch or individual CSP using traditional physical analyses has resulted in a loss of time and financial resources for the pharmacies. Therefore, there is a need for methods and systems for testing CSPs that avoid the expense and other problems associated with the use of traditional physical analyses for testing CSPs.

SUMMARY OF THE INVENTION

One aspect of the invention is an interactive method of obtaining requests for the analysis of a sample having an unknown concentration or purity, performing an analysis of the sample to determine the concentration or purity of the sample having an unknown concentration and/or purity, determining the concentration or purity, or both, of the sample having an unknown concentration or purity from the analysis, and reporting the determined concentration or purity of the sample to the requester through an electronic medium. The sample can be a compounded sterile or non-sterile preparation.

Another aspect of the invention is obtaining a request to confirm a concentration of a sample having an intended concentration.

In one aspect of the invention a method for organizing, monitoring and reporting results of analysis of samples through an electronic network is described that comprises allowing a user to perform at least one operation through an electronic network selected from a group of operations consisting of requesting at least one analysis of at least one sample through the electronic network, tracking the analysis of the sample through the electronic network, monitoring the analysis of the sample through the electronic network, retrieving the results of the analysis of the sample through the electronic network, or any combination thereof, as well as conducting at least one analysis of the sample, monitoring the analysis of the sample, organizing the results of the analysis, storing the results of the analysis in at least one database, allowing the input and storage of analytical data into the database, wherein the analytical data comprises a library of acceptable ranges of results.

In another aspect of the invention a method of performing an analysis of a sample having a predetermined concentration and purity, obtaining data regarding the analysis of the sample having a predetermined concentration and purity, storing the data in a retrievable form, performing an analysis of a sample having an unknown concentration and/or purity; obtaining data regarding the analysis of the sample having an unknown concentration and/or purity, comparing the data regarding the analysis of the sample having an unknown concentration and/or purity to the data regarding the analysis of the sample having a predetermined concentration and purity which was stored in a retrievable form; and determining a concentration and/or purity of the sample having an unknown concentration and purity through the comparison. The sample can be a compounded sterile or non-sterile preparation. The method can be interactive.

BRIEF DESCRIPTION OF THE DRAWINGS

FIG. 10 is a sample testing request screen;

FIG. 11 is a sample tracking screen;

DESCRIPTION OF THE PREFERRED EMBODIMENTS

Figure 1:
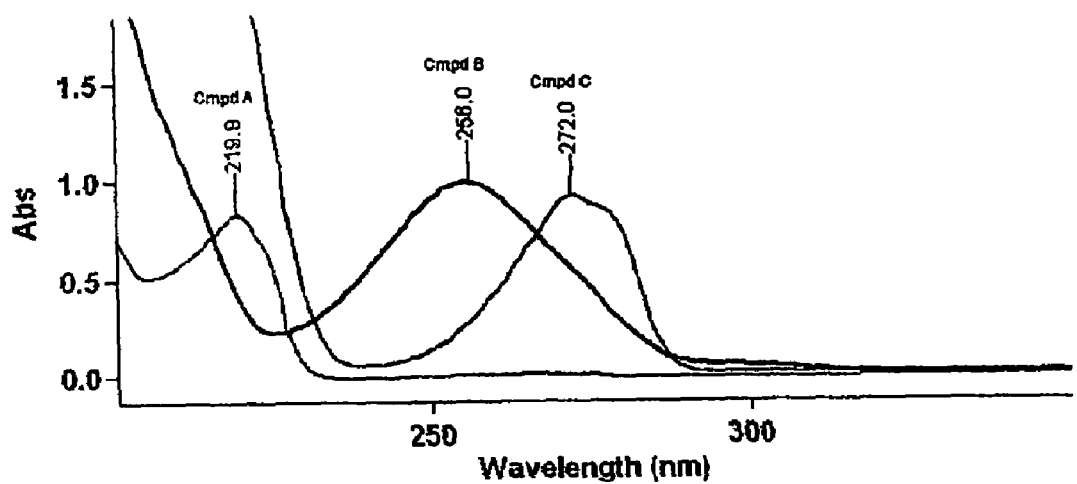
FIG. 1 is a graph illustrating the UV light absorbance curves of three different compounds.

New and useful methods for verifying the identity and determining or the confirming the presence of a target or active ingredient as well as potency, purity and presence of contaminants, microbial, endotoxin and particulate matter (referred to hereinafter as "purity") in a mixture of ingredients, and a series of integrated systems and processes for the requesting, performing, organizing, monitoring and reporting of such analyses and related metadata through an electronic network have been discovered.

In each embodiment or aspect of the invention for purposes of clarity and brevity, the mixture of ingredients that is the subject of the method can be referred to as a sample having an unknown concentration or purity. This reference to the sample, when used hereinafter, is intended to include samples having only an unknown concentration or having only an unknown purity or having both an unknown concentration and unknown purity. It also is intended to include a sample having an intended concentration that is analyzed to confirm that the sample indeed includes the intended concentration, within an acceptable deviation. The sample having an unknown concentration or purity can be a compounded sterile or non-sterile preparation. However, the methods have broader application and can be used to analyze a sample of any type.

One representative embodiment of the invention is a method of conducting a business comprising obtaining requests for the analysis of a sample having an unknown concentration or purity, performing an analysis of the sample to determine the concentration or purity of the sample having an unknown concentration or purity, determining the concentration or purity of the sample having an unknown concentration or purity from the analysis, and reporting the determined concentration or purity of the sample to the requester through an electronic medium. The requester can interact with the method.

In one representative embodiment an interactive method comprises allowing a requester to perform, through an electronic network, at least one operation selected from a group of operations comprising requesting at least one analysis of at least one sample through the electronic network, tracking the analysis of the at least one sample through the electronic network, monitoring the analysis of the at least one sample through the electronic network, retrieving the results of the analysis of the at least one sample through the electronic network, or any combination thereof, and allowing a service provider to conduct at least one analysis of the at least one sample, monitor the at least one analysis of the at least one sample, organize the results of the at least one analysis, store the results of the at least one analysis in at least one database, allow the input and storage of analytical data into the at least one database, wherein the analytical data comprises a library of acceptable ranges of results.

In the various aspects or embodiments of the invention, the term requester is intended to include, but not be limited to, any requester of, customer of, member of or subscriber to, the methods of the present invention who requests an analysis of a sample.

In the various aspects or embodiments of the invention, the requester provides the samples having an unknown concentration of purity.

In another representative embodiment of the invention the method comprises performing an analysis of a sample having a predetermined concentration or purity; obtaining data regarding the analysis of the sample having a predetermined concentration or purity; storing the data in a retrievable form; receiving a request for performing an analysis of a sample having an unknown concentration or purity; obtaining data regarding the analysis of the sample having an unknown concentration or purity; comparing the data regarding the analysis of the sample having an unknown concentration or purity to the data regarding the analysis of the sample having a predetermined concentration or purity which was stored in a retrievable form; determining a concentration or purity of the sample having an unknown concentration or purity through the comparison; and reporting the determined concentration or purity of the sample having an unknown concentration or purity to the requester, generally through an electronic medium.

In one representative embodiment of the invention, conducting the analysis of the samples comprises comparing the analytical data obtained from the analysis of the sample having an unknown concentration or purity with historical analytical data regarding analyses of samples having a known concentration or purity stored in the database. The analytical data includes a library of predetermined ranges of concentration or purity. The predetermined ranges can be expressed as curves based upon a spectrographic data obtained through spectrographic analysis of samples having known concentrations or purities. Generally, each individual result of the analysis of the sample having an unknown concentration or purity is compared with the library of predetermined ranges. The library may include, but is not limited to pharmaceutical, organic or biochemical materials spanning a normal process range.

In one representative embodiment of the invention, the analyses are spectrographic analyses to determine energy absorbance by the contents of the samples.

In one representative embodiment of the invention, the method and system of the invention integrate the use of near-infrared ("NIR") energy absorbance technology within an electronic system and business process for maintaining the results of the analyses for future use. The analysis of samples is conducted using NIR energy absorbance technology.

In one representative embodiment of the invention, the method and system of the invention integrate the use of ultraviolet (UV) light absorbance technology within an electronic system and business process for maintaining the results of the analyses for future use. The analysis of samples is conducted using UV light absorbance technology.

In one representative embodiment of the invention, the method and system of the invention integrate the use of a combination of NIR energy absorbance technology and ultraviolet (UV) light absorption technology within an electronic system and business process for maintaining the results of the analyses for future use. The sample analysis is conducted using both NIR energy absorbance and UV light absorbance technology.

In one representative embodiment of the invention, the analysis of the sample is monitored before, during and after the analysis. The results are generally integrated into a broader database that comprises a library of acceptable ranges expressed as curves derived from spectrographic analyses. The spectrographic analyses can be performed by UV light absorbance technology, NIR energy absorbance technology or a combination thereof. Furthermore, the analysis can be performed by other technologies such as Raman, IR, TD-NMR, TeraHertz, x-ray or so forth. The integration of the systems into a larger body of data and results enables future use of the data and results for further analysis.

In some cases, independent, or third party analyses of samples of known or unknown concentration and purity are introduced into the broader database, so as to establish a standard of measurement for similar future analysis. The incorporation of this data and use of the data as a reference will ultimately establish new component constituents. Translation of the resultant data from the integrated testing equipment using at least one program, instruction or process, especially those electronic in nature, into a systematic series of outcomes and results, which are transmitted through the network for many purposes, including coordination, efficiency, analysis and improvement within the business process and component processes, especially through electronic means.

In one representative embodiment of the invention, the database, which includes the results of the analyses, as well as other data, will be hosted on a web server or other similar communication network component, which will permit anyone with access to the Internet to access the system and perform certain methods of the invention. In certain embodiments, the methods and systems of the invention are adapted to be programmed to allow any authorized entity, which can include the service provider as well as an authorized requester, to participate in the process through the web server. The systems and methods are adapted to identify the authorized entity, and to request analyses or other tests to be requested through the web server. The authorized entity may also ascertain the scope of the broad database for a determination of the constituent entities for which a standard is established. In one embodiment of the invention, a notification of the results is sent to at least one pre-determined entity.

In one particular application of the invention, samples are analyzed for concentration and purity. More specifically, samples are analyzed for concentration, as well as to determine if they are sufficiently pure, to establish whether the pharmaceuticals fall within parameters set forth by the regulatory bodies. Specifically, the desired concentration of a target or active ingredient as well as presence or concentration of pathogens or other contaminants is determined using traditional physical analytical techniques, as well as UV light absorbance and NIR energy absorbance technology, which produce spectral data that can be stored electronically for later comparison to other spectral graphs. The results of both analyses are added to a database for future use, which also contains the concentration and purity parameters set forth by the regulatory bodies.

In various aspects and embodiments of the invention, the sample to be analyzed is a compounded sterile preparation ("CSP") or non-sterile preparation.

The methods of the invention can be utilized to eliminate the time consuming task of testing each sample, for example a CSP, produced by a pharmacy using traditional physical analysis, which reduces both labor and production costs. In accordance with this particular method of the invention, once a particular CSP is analyzed using traditional physical analysis, NIR technology or UV technology, the same CSP can simply be tested for compliance with the regulatory bodies' concentration or purity parameters using UV or NIR technology, which is much less labor intensive and time consuming when compared to traditional physical analysis. The spectrographical data stored in the database from the initial UV or NIR analysis is compared to the spectrographical data gathered from the sample being tested using UV or NIR technology.

The spectral data is used to develop an equation that is then used to calculate the concentration of a sample based upon the absorbance of the sample at a predetermined wavelength in nanometers (nm) or wavenumber in reciprocal centimeters ($cm^{-1}$), as explained below.

Accordingly, the CSP can be tested for concentration and purity quickly and effectively after initial testing of the pharmaceutical using traditional physical analysis. The information obtained from subsequent analyses using UV or NIR technology is also added to the database, further expanding the library of known concentration and purity parameters. The database is continually updated and expanded, as the results of every analysis is stored and maintained for future use.

By way of further example, an electronic database of spectrographical data is established using the results of analysis of samples of known concentration or purity. This spectrographical data can be obtained by using UV light absorbance technology, NIR energy absorbance technology or both. Generally, UV technology is used to determine the spectrographical data of samples having low concentrations of constituents, for example, samples having an estimated concentration of less than approximately 10 mg/ml of active or target constituent. One example of equipment used to perform a UV analysis is the Cary 50 manufactured by Varian, Inc., Palo Alto, Calif. Those samples having an estimated concentration of greater than approximately 10 mg/ml generally are analyzed by NIR technology. One example of equipment used for performing the NIR analysis is the Vector 22/N manufactured by Bruker Optics, Billerica, Mass.

FIGS. 1 through 4 illustrate graphs that reflect UV spectra and NIR spectra. Both technologies can be used to identify and quantify a target ingredient or constituent of a sample. The respective graphs indicate energy (light) absorbance as the vertical coordinate on the left, and wavelength or wavenumber as the horizontal coordinate across the bottom.

FIG. 1 illustrates UV light absorbance curves of three different compounds. As shown, Compound A exhibits maximum absorbance at a UV wavelength of 219.9 nm; Compound B exhibits maximum UV absorbance at 256.0 nm; and Compound C exhibits maximum UV absorbance at 272.0 nm. Hence, FIG. 1 illustrates the fact that three different compounds have three different, yet unique, absorbance curves.

Figure 2:
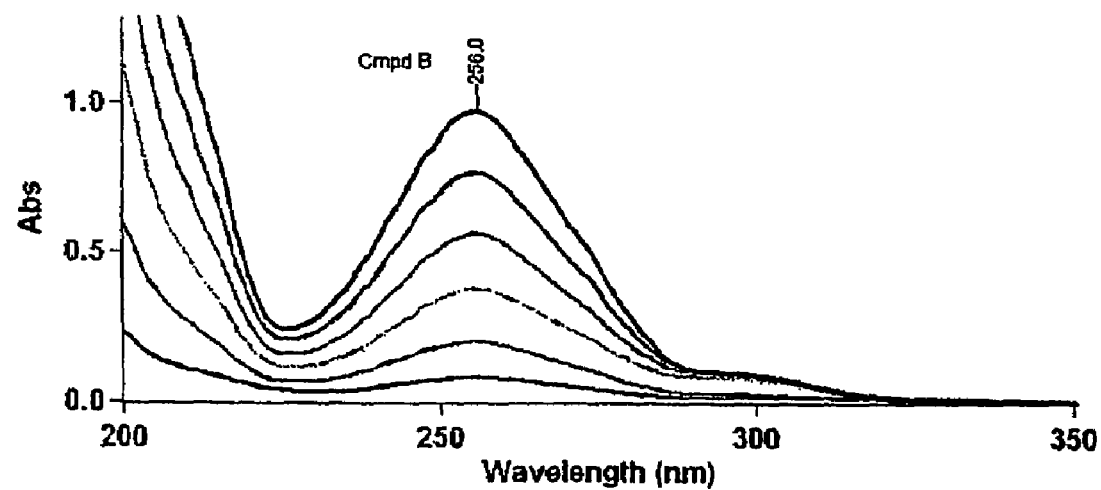
FIG. 2 is graph illustrating the UV light absorbance curves of six different concentrations of a single target constituent.

FIG. 2 illustrates UV absorbance waves of various concentrations of Compound B. In the illustrated graph, six (6) different concentrations of Compound B were analyzed. It will be noted that, despite the concentration of Compound B, maximum UV absorbance of each of the six samples occurs at 256.0 nm, confirming the presence of target constituent Compound B.

Figure 3:
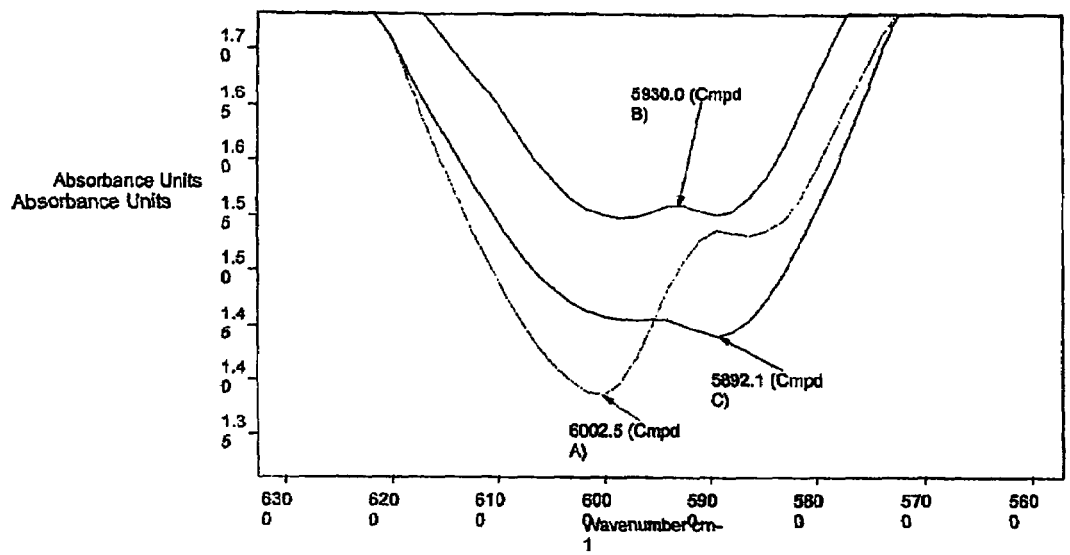
FIG. 3 is a graph illustrating the NIR energy absorbance curves of the three different compounds.
Figure 4:
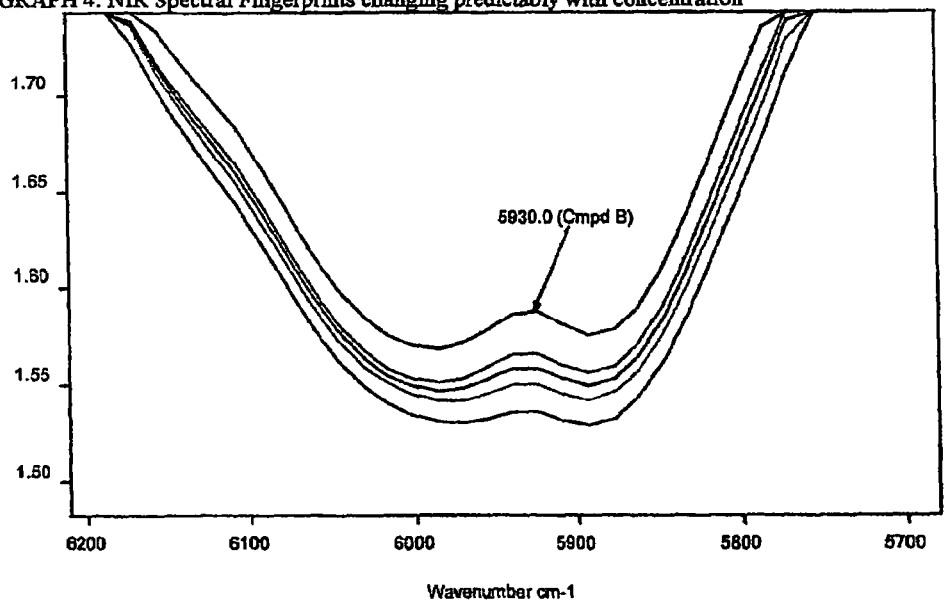
FIG. 4 is a graph illustrating the NIR energy absorbance curves six different concentrations of single target constituent of FIG. 2.

Similarly, FIGS. 3 and 4 illustrate NIR energy absorbance curves for Compounds A, B and C. As seen in FIG. 3, maximum energy absorbance of Compound A occurs at 6002.5 wavenumber ($cm^{-1}$) Compound B exhibits maximum absorbance at 5930.0 wavenumber ($cm^{-1}$) and Compound C exhibits maximum absorbance at 5892.1 (wavenumber ($cm^{-1}$)

FIG. 4 illustrates the NIR energy absorbance curves of Compound B. In FIG. 4, five (5) different dilutions of Compound B are analyzed, with maximum absorbance confirmed at 5930.0 wavenumber ($cm^{-1}$)

Both technologies, therefore can be used to identify and quantify a known compound. The choice of technology used depends upon the concentration of the compound and the located of the absorbance peaks.

Generally speaking, in use, several concentrations are made of samples of known target constituent and purity. These samples having known target constituents and concentration are analyzed by the UV or NIR technology and a spectrographic graph of absorbance is obtained of the type illustrated by FIGS. 2 and 4. The NIR or UV absorbance peaks should coordinate for each dilution. This spectrographic data is stored in a database.

Subsequent analyses are performed on samples of an expected target constituent having an unknown concentration or purity. Spectrographic data in the form of absorbance curves derived from diluted or undiluted samples having an unknown concentration or purity are obtained, also similar to those shown in FIGS. 2 and 4. Spectrographical data obtained by the subsequent analysis of samples of unknown concentration or purity can be compared to the spectrographical data stored in the database.

Using a suitable algorithm, an equation is derived from the spectral curves using the energy (light) absorbance value at single or multiple wavenumbers (lengths) and the known concentration value of each sample. The equation is applied to the spectrographic absorbance curves of the samples of unknown concentration, and the concentration of the target constituent in the provided sample is derived. Hence, a determination of the concentration or purity of the sample of having an unknown concentration or purity is determined from the comparison of its spectrographical data to the spectrographical data of samples having known concentrations or purities and application of the equation. The comparison, therefore, can include the step of applying the appropriate equation.

Furthermore, as can be appreciated from considering FIGS. 1 and 3, it is possible to identify and verify the target constituent. These spectrographic curves demonstrated that compounds have a unique absorbance curve. The spectrographic curves that are unique to any given compound, for example, can be considered to be a spectral fingerprint of that compound. As illustrated, FIGS. 1 and 3 show that Compounds A, B and C, for example, have their own spectral fingerprint. Consequently, if the sample of unknown concentration or purity includes a target constituent that is supposed to be Compound A, the analysis can confirm that the target constituent is indeed Compound A.

It will be appreciated that NIR analysis of appropriate samples has an advantage in certain circumstances over that of UV analysis. While both technologies can provide a determination of concentration or purity of the target constituent, of an unknown or unconfirmed concentration, the spectrographic data of the sample produced through the use of NIR technology is better used to identify the target constituent, as well as the concentration. That is, the spectrographic data produced by NIR technology provides a much more specific spectral fingerprint that is unique to the target constituent. This primarily is a result of the fact that UV is an electronic-type transition (within a molecule) and there are a limited number of peaks due to specific "chromophores", such as a phenyl or benzene ring in the structure. NIR, however, is a vibrational-type transition that "sees" all the atoms within the molecule. This leads to a much richer spectrum, giving a more detailed compound specific fingerprint than UV.

In one embodiment of the invention, the combination of both NIR and UV can be used to analyze a single sample. Not only will the analysis determine the concentration of the target constituent, it also will confirm that the target constituent is indeed the desired or suspected target constituent. The combination of technologies allows the testing of samples having a broader range of concentrations and constituents. Returning to the example discussed immediately above, if the target constituent is assumed to be Compound A, for example, in an intended concentration, the service provider can use a combination of NIR and UV technologies confirm that the target constituent is Compound A from its NIR fingerprint and also determine the concentration through the comparison of UV or NIR absorbance curves and the application of the equation or vice versa, depending upon the characteristics of the target constituent.

In another aspect of the invention, the method includes the analysis of samples of unknown concentration or purity for the presence of contaminants, including microbial, endotoxin and particulate matter in a mixture of ingredients. These determinations can be made by conventional analyses known to the art or can be a component of the spectrographic analysis.

By way of example, the presence of particulate matter and other contaminants can be determined by such processes as microscopic identification and/or light obscuration. Contamination by microbial organisms can be identified through the traditional methods, such as microbial identification by propagation in appropriate microbial media and under appropriate environmental conditions, or by determining the presence of ATP resulting from bacterial respiration using spectral and/or chromogenic means. Endotoxins can be identified using traditional test methods such as the rabbit test, gel clot test, kinetic or endpoint chromogenic or turbidometric methods, or by using recombinant technologies, or by other spectrophotometric means.

Figure 5:
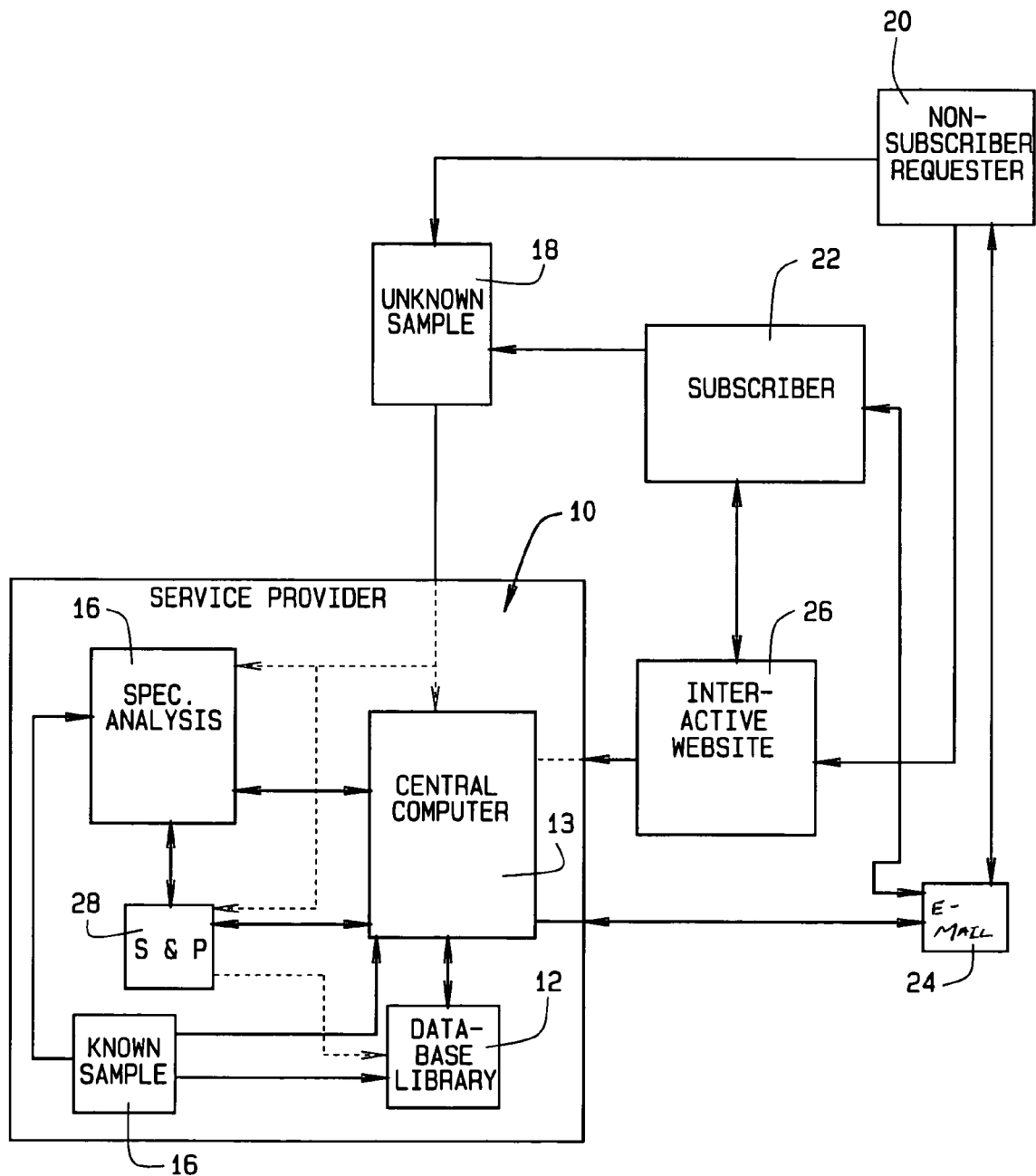
FIG. 5 is a block diagram illustrating an exemplary embodiment of a method of the present invention.

One aspect of the invention is a method of conducting a business employing the methods of the present invention. A representative, interactive embodiment of such is provided by FIG. 5. A service provider 10 provides the service of developing and maintaining a library of spectrographical data of samples of known constituents, concentrations and purity stored in a retrievable format in database 12. It will be appreciated that database 12 is operatively associated with a computer, such as central computer 13. The database 12 can be physically maintained at any site, such as a remote or portable computer as well as computer 13, which may be located on the service provider's site. In any event, the computer can be appropriately programmed to maintain the database.

The service provider 10 also provides the service of determining or obtaining the spectrographical data of samples to store in the database 12. That is, the service provider 10 performs spectrographic analysis 14 using the NIR or UV technologies, or other technologies such as Raman, IR, TD-NMR, TeraHertz, x-ray, described above, and obtains spectrographic data from samples having a known concentration or purity 16. The service provider also can obtain spectrographical data to store in the database from third parties or regulatory agencies (not shown). It will be appreciated that the database is constantly expanding.

The service provider 10 receives requests from for the analysis of a sample 18 having a concentration or purity of a target constituent that is unknown or not precisely or accurately known or not confirmed, as described above.

The request may come from a random or occasional requester 20 or from a subscriber to the service 22. The subscriber also may be referred to as a member. The occasional requester and the member also can be referred to as customers. In one aspect of the invention, the requester 20 or subscriber 22 can make the request electronically for example, through electronic mail 24 or an interactive website 26 which is hosted on an appropriate server, either by a third party provider or through computer 13, as will be explained in more detail below. Computer 13 is operatively associated with the website 26 or e-mail 24 or both. In any event, the occasional requester or subscriber generally physically provides the sample 18 to be analyzed. The sample 18 can be conveyed to the service provider by any acceptable means, for example direct conveyance, courier or proprietary shipper, such as FedEx® or United Parcel Service. The information regarding shipping and receipt of the specimen is entered into computer 13, so that it can be tracked, as described below.

The service provider 10 runs a spectrographical analysis 14 of the provided sample, either by using UV technology, NIR technology, or both. The spectrographical data of the sample obtained from spectrographical analysis 14 is compared to the database 12 of stored spectrographical data for that target constituent to determine the concentration or purity of the sample through the comparison. The determination made through the comparison and application of the appropriate equation, as described above.

Furthermore, the service provider 10 performs the tests for contaminants, including microbial, endotoxins and particulate matter in a mixture of ingredients, referred to in FIG. 1 as analysis for sterility and purity 28. The data from the sterility and purity testing is stored in a retrievable form in computer 13 and/or associated database 12. These analyses for sterility and purity also can be performed off-site and the data integrated into the system.

The service provider can confirm that the target constituent is indeed the intended target constituent based upon the unique spectral fingerprint of the constituent, as explained above.

The determined concentration and sterility and purity of the sample of unknown concentration or purity, as well as the confirmation of the presence of the target constituent, then is communicated to the requester 20 or subscriber 22. The transmission can be generally be made electronically, for example, via e-mail 24. However, such electronic transmission can be through other electronic media such as telephone or facsimile or the like. Moreover, the results can be communicated by more mundane methods, such as oral notification or mail or the like.

In another embodiment of the invention, the results of the analyses are obtained through the interactive website 26. In this embodiment, a random requester 20 may have limited access to the interactive website. A subscriber 22, on the other hand, can have access to a personal account. This account will allow the subscriber to request an analysis, as set out above, and also to track the shipping and receipt of the sample, progress of the analysis, determination and posting of the results, through the interactive website. The results of analyses of the subscriber's samples are stored and accessible through the account. Consequently, for a subscription fee, the subscriber can access a secure website request analysis, track the analysis and obtain the requested analysis results in real time, as it is posted on the website 26.

Figure 6:
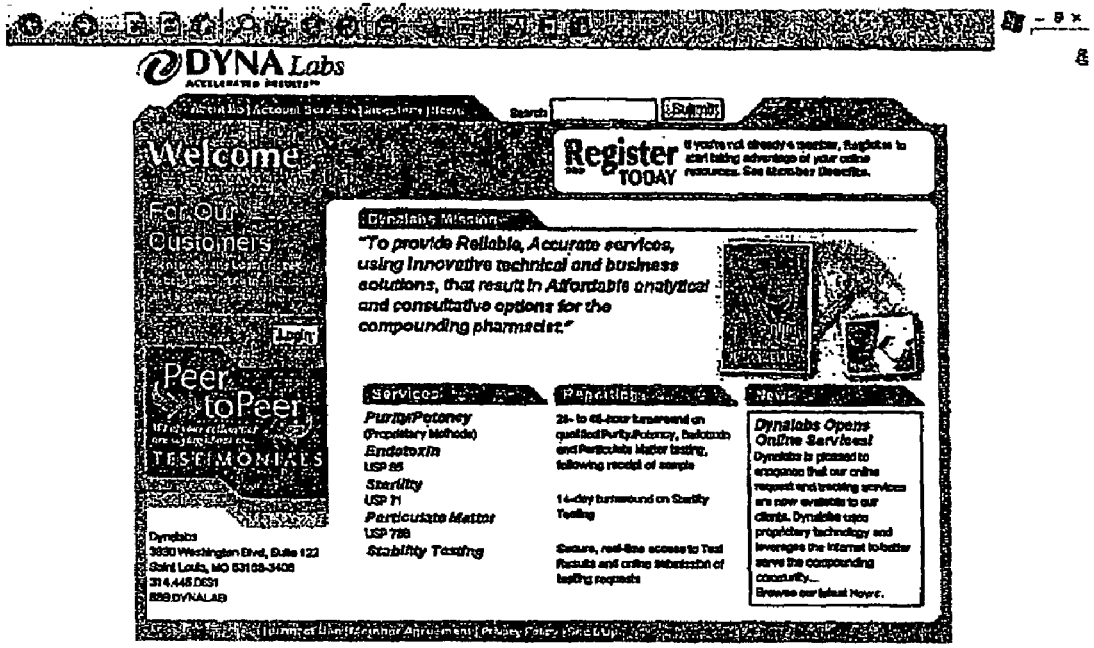
FIG. 6 is an interactive website introductory screen for access by a potential subscriber to the method of the present invention.
Figure 7:
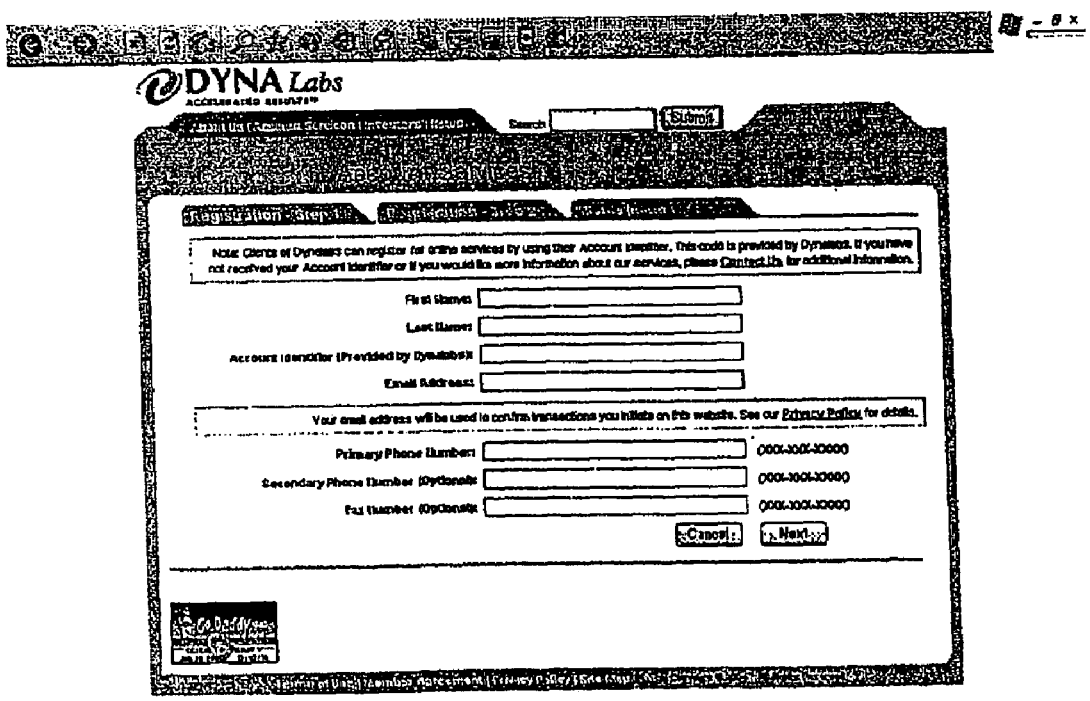
FIG. 7 is a website screen including a registration form.

FIGS. 6 through 13 are representative embodiments of interactive website computer screens employed in one embodiment of the present invention. FIG. 6 is an introductory screen that lists services provided according to the invention, by the service provider. At this point, the potential subscriber can work with a service provider representative to set up an account. Once the subscriber account is established, the subscriber can access the registration screen FIG. 7 to register.

Figure 8:
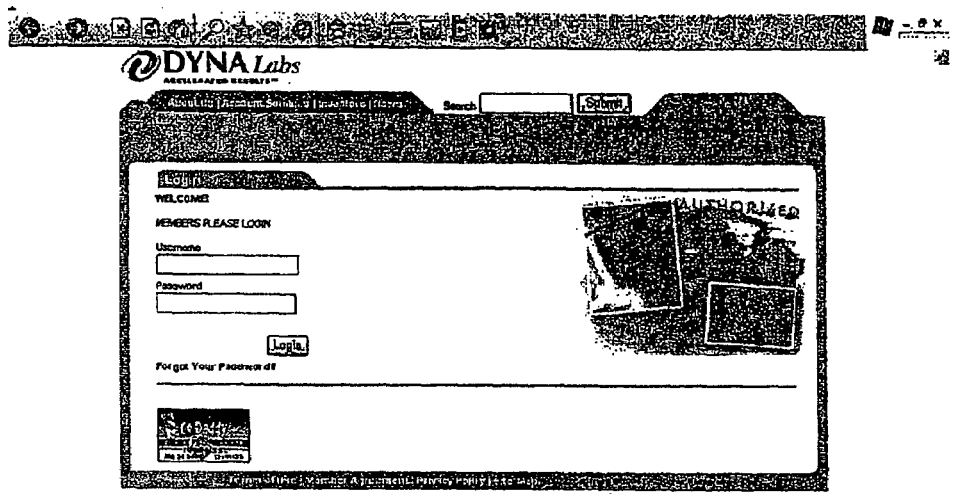
FIG. 8 is a website log on screen.
Figure 9:
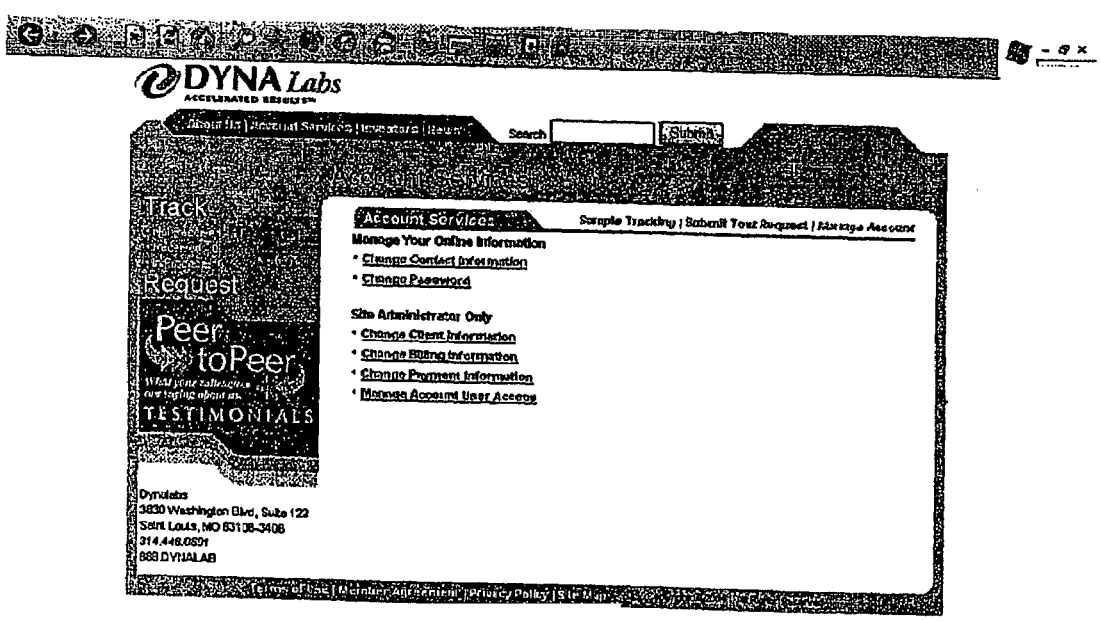
FIG. 9 is an account services screen.
Figure 12:
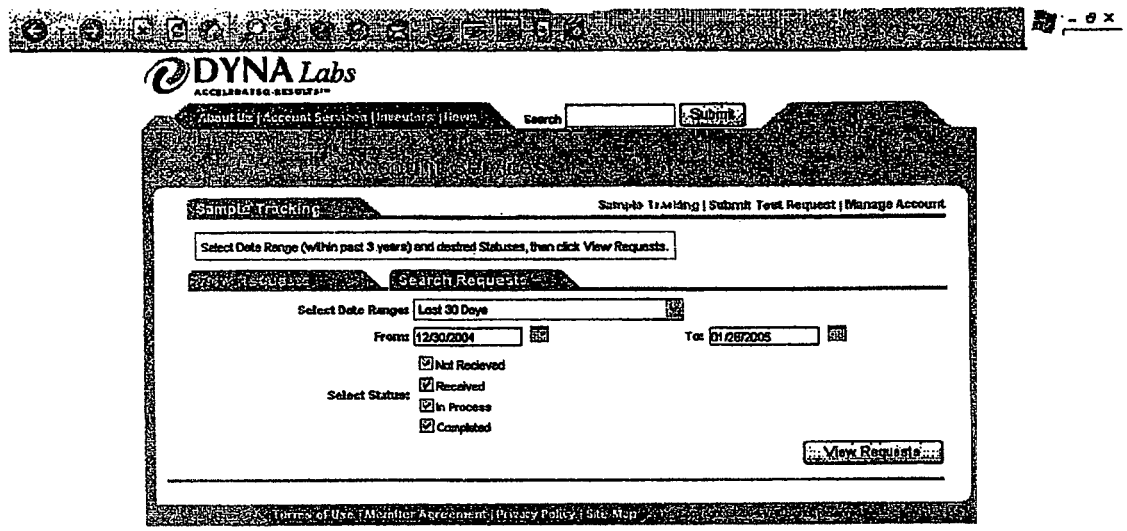
FIG. 12 is an additional sample tracking screen.

After the subscriber is registered, he or she can gain access to the system through the screen of FIG. 8, which is a typical log on screen. As will be appreciated, the system is secure, and a password is required for access. Once the subscriber accesses the system, he or she can proceed to a listing of account services, as illustrated in FIG. 9. This feature allows the subscriber to manage the account. The subscriber can access the desired account service by a simple computer mouse click.

Figures 10, 11:
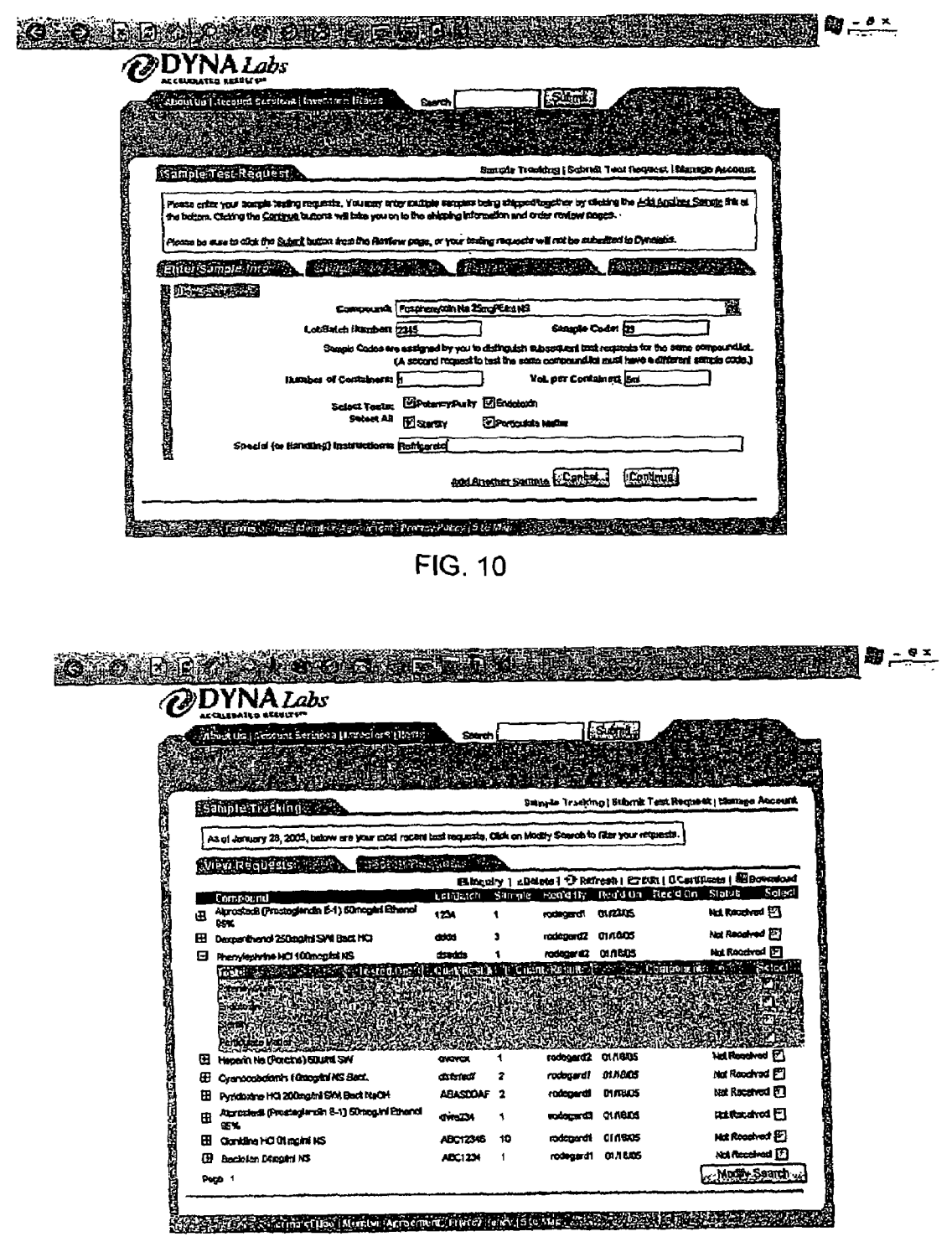

FIG. 10 is a representative embodiment of an interactive screen that allows the subscriber to submit a sample for analysis. This screen allows the subscriber to specify testing requests. The physical samples are shipped separately. This screen also allows access to shipping and receiving information and order review pages.

FIG. 11 is a representative embodiment of one sample tracking screen. The subscriber can track the submitted sample through shipping, receipt, testing stages and view results. FIG. 2 illustrates a sample tracking screen that allows the subscriber to track and trend data over time or by selected criteria, such as product, testing, analysis and so forth.

Figure 13:
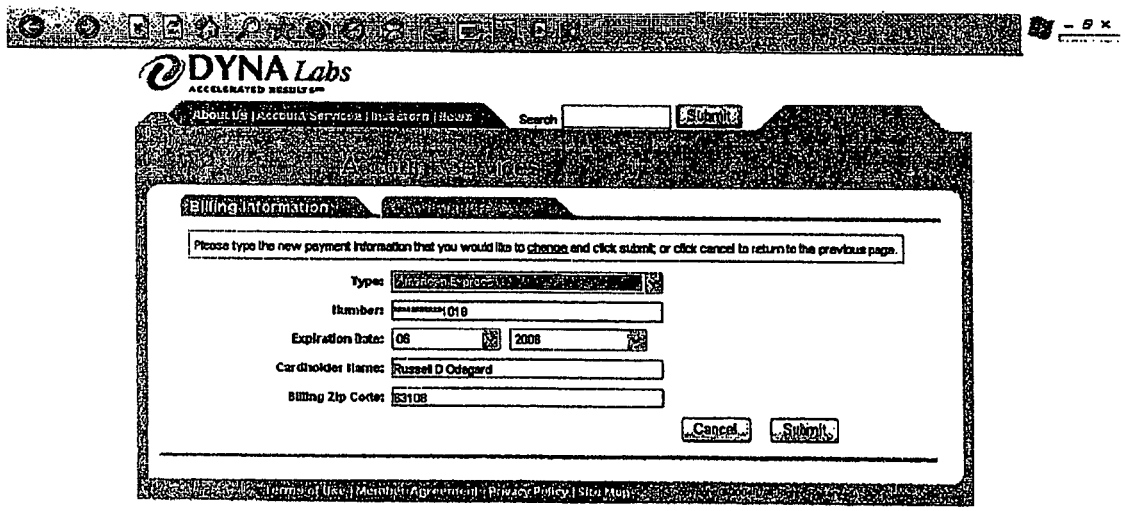
FIG. 13 is a subscriber payment screen.

Finally, the service provider generally charges a fee for the analysis of the sample from the requester or a subscription fee from a subscriber. FIG. 13 is an embodiment of a subscriber (customer) billing screen that allows the subscriber to pay for the requested services on line. The subscriber also would have the capability to track and trend their financial or payment data.

The above-described screens are illustrative of the type of screens that can be employed in the methods of the present invention. However, any embodiment of a computer screen or web page is acceptable and included within the scope of the invention.

It is one aspect of the invention, therefore, that allows the subscriber to request at least one analysis of at least one sample through the electronic network, track the analysis of the at least one sample through the electronic network, monitor the analysis of the at least one sample through the electronic network, retrieve the results of the analysis of the at least one sample through the electronic network; analyze trends through the electronic network, pay for services through the electronic network, or any combination thereof.

In another aspect of the invention the spectrographical data obtained from the subscriber's sample and from the relevant sample of known concentration or purity are added to the database for future use in analysis for the subscriber or other requesters seeking a determination of the identity, concentration or purity of the same target constituent. Consequently, through the provision of the services, the service provider 10 enhances the performance and versatility of the process by expanding the library of spectrographic data in database 12.

In one aspect of the invention, the requester or subscriber can be an administrative agency or professional entity such as the Food & Drug Administration, the D.E.A., or the United States Pharmacopoeia (U.S.P.).

The foregoing method of doing business is operated through an electronic network and includes a computer, such as computer 13 configured with a set of application programs embodied on a computer readable medium utilized to effectuate the methods of present invention including, but not limited to, accepting requests, analyzing samples, sample tracking, compiling databases, performing data comparisons, reporting results either through electronic mail or by posting on a website for subscriber access.

The methods of the present invention also include a data processing system for managing a process for determining the concentration or purity of a sample having an unknown concentration or purity including a computer processor for processing data; and computer software configured to perform the functions of a.) receiving and processing a request for an analysis of a sample having an unknown concentration or purity; b.) determining spectrographical data of a concentration or purity of a sample having a known concentration or purity; c). storing in a database the spectrographical data of a concentration or purity of a sample having a known concentration or purity; d.) determining spectrographical data of a concentration or purity of a sample having an unknown concentration or purity; e.) comparing the determined spectrographical data of the concentration or purity of the sample having an unknown concentration or purity to the spectrographical data in the database of spectrographical date of the concentration and purity of samples having a known concentration or purity; f). determining the concentration or purity of the sample having an unknown concentration or purity from the comparison of the spectrographical data in the database of spectrographical data of the concentration and purity of samples having a known concentration or purity; g.) determining the purity and sterility of the sample having an unknown concentration or purity; h.) communicating the determined concentration or purity and sterility of the sample having an unknown concentration or purity to the requester or subscriber through an electronic medium; and h.) monitoring one or all of the above activities; and h.) any other function required by the methods of the present invention.

As one skilled in the art will appreciate, the order of the steps of the methods described herein is not critical. The method steps described may be performed in various orders. More over, the steps may be performed at different times, for example, the steps of determining spectrographical data of a concentration or purity of a sample having a known concentration or purity or storing in a database the spectrographical data of a concentration or purity of a sample having a known concentration or purity may be performed well in advance of other of the steps. Moreover, steps such as these could be performed once only, while others of the steps performed for each new requested analysis.

The described methods can be used to analyze compounded sterile pharmaceuticals (CSPs) or non-sterile compounds, as set out. However, it will be appreciated that the methods of the present invention can be used to analyze the concentration or purity of other substances or compounds without departing from the scope of the invention.

In view of the above, it will be seen that all the objects and features of the present invention are achieved, and other advantageous results obtained. The description of the invention contained herein is illustrated only, and is not intended in a limiting sense.

What is claimed is:

1. A method of providing a service to a requester of determining the concentration of at least one constituent in an extemporaneously compounded sample having an unknown concentration for the requester, comprising the steps of:

accepting a request from the requester for determining a concentration of at least one constituent in an extemporaneously compounded sample having at least one constituent at an unknown concentration;

performing a spectrographic analysis of a sample having the at least one constituent at at least one predetermined concentration, said spectrographic analysis providing identifying data for a range of concentrations of the at least one constituent;

storing the obtained spectrographic analysis of the sample having the at least one constituent at at least one predetermined concentration in a retrievable form in a database comprising identifying data of ranges of concentrations of at least one constituent;

performing a spectrographic analysis of the extemporaneously compounded sample having at least one constituent at an unknown concentration, said spectrographic analysis providing identifying data for at least one concentration of the at least one constituent;

comparing the spectrographic analysis of the extemporaneously compounded sample having at least one constituent at an unknown concentration to the spectrographic analysis of the sample having the at least one constituent at at least one predetermined concentration stored in a retrievable form;

mathematically calculating a concentration of the at least one constituent in the extemporaneously compounded sample having at least one constituent at an unknown concentration from the comparison of the recited spectrographic analyses data; and transmitting the calculated concentration of the at least one constituent of the extemporaneously compounded sample having at least one constituent at an unknown concentration to the requester.

2. The method of of claim 1 further comprising the step of compiling a database of determined spectrographic analyses of samples having at least one known constituent at at least one known concentration.

3. The method of claim 2 wherein each recited spectrographic analysis expands the database of determined spectrographic analyses of samples having at least one known constituent at at least one concentration.

4. The method of claim 1 wherein the step of transmitting the calculated concentration of the at least one constituent in the extemporaneously compounded sample having at least one constituent at an unknown concentration to a requester comprises transmitting the calculated concentration through an electronic medium.

5. The method of claim 4 wherein the electronic medium further comprises electronic mail.

6. The method of claim 4 wherein the electronic medium further comprises an interactive website.

7. The method of claim 1 wherein the step of performing a spectrographic analysis of a sample having the at least one constituent at at least one predetermined concentration further comprises performing a spectrographic analysis using NIR energy absorbance technology.

8. The method of claim 1 wherein the step of performing a spectrographic analysis of a sample having the at least one constituent at at least one predetermined concentration further comprises performing a spectrographic analysis using UV light absorbance technology.

9. The method of claim 1 wherein the step of performing a spectrographic analysis of a sample having the at least one constituent at a predetermined concentration further comprises performing a spectrographic analysis of a sample having a predetermined concentration using NIR energy absorbance technology and UV light absorbance technology.

10. The method of claim 1 wherein the step of performing a spectrographic analysis of an extemporaneously compounded sample having at least one constituent at an unknown concentration further comprises performing a spectrographic analysis using NIR energy absorbance technology.

11. The method of of claim 1 wherein the step of performing a spectrographic analysis of an extemporaneously compounded sample having at least one constituent at an unknown concentration further comprises performing a spectrographic analysis using UV light absorbance technology.

12. The method of claim 1 wherein the step of performing a spectrographic analysis of an extemporaneously compounded sample having at least one constituent at an unknown concentration further comprises performing a spectrographic analysis using NIR energy absorbance technology and UV light absorbance technology.

13. The method of claim 1 further comprising the step of analyzing the extemporaneously compounded sample having at least one constituent at an unknown concentration to determine the sterility and purity of the sample.

14. The method of claim 1 wherein the at least one constituent of the extemporaneously compounded sample having at least one constituent at an unknown concentration is a known constituent.

15. The method of claim 1 wherein the at least one constituent of the extemporaneously compounded sample having at least one constituent at an unknown concentration is unknown.

16. A method of identifying at least one constituent and determining the concentration thereof, in a compounded sample having at least one unknown constituent at an unknown concentration comprising the steps of:
performing a spectrographic analysis of a compounded sample having at least one unknown constituent at an unknown concentration;
obtaining data regarding the spectrographic analysis of the compounded sample having at least one unknown constituent at an unknown concentration, said data comprising at least one energy absorbance concentration curve;
comparing the at least one energy absorbance curve resulting from the spectrographic analysis of the compounded sample having at least one unknown constituent at a unknown concentration to at least one energy absorbance curve resulting from a spectrographic analysis of at least one sample having at least one predetermined constituent at at least one predetermined concentration which was stored in a retrievable form;
identifying the at least one unknown constituent in the compounded sample having an at least one unknown constituent at an unknown concentration from the energy absorbance curve obtained from the spectrographic analysis of the compounded sample and mathematically calculating the concentration thereof from data derived from the recited comparison of the energy absorbance concentration curves; and
transmitting the identity of the at least one unknown or the calculated concentration thereof or both to a requester.

17. The method of claim 16 comprising the further step of transmitting the identity of the at least one unknown constituent or the calculated concentration or both said identity and said calculated concentration to the requester through an electronic medium.

18. The method of claim 17 wherein the step of transmitting the identity of the at least one unknown constituent or the calculated concentration or both the identity of the at least one unknown constituent and the calculated concentration through an electronic medium is performed by electronic mail.

19. The method of claim 17 wherein the step of transmitting the identity of the unknown constituent and the calculated concentration or both the identity and the calculated concentration is performed through a website posting.

20. The method of claim 16 further comprising the steps of performing a spectrographic analysis of at least one sample having at least one predetermined constituent at at least one predetermined concentration using near-infrared energy absorbance technology and storing said spectrographic analysis in a retrievable form.

21. The method of claim 16 further comprising the steps of performing a spectrographic analysis of the at least one sample having at least one predetermined constituent at at least one predetermined concentration using ultraviolet light absorbance technology and storing said spectrographic analysis in a retrievable form.

22. The method of claim 16 further comprising the steps of performing a spectrographic analysis of a sample having at least one predetermined constituent at at least one predetermined concentration using near-infrared energy absorbance technology and ultraviolet light absorbance technology and storing said spectrographic analysis in a retrievable form.

23. The method of claim 16 wherein the spectrographic analysis of a compounded sample having at least one unknown constituent at an unknown concentration is conducted using near-infrared energy absorbance technology.

24. The method of claim 16 wherein the spectrographic analysis of a compounded sample having at least one unknown constituent at an unknown concentration is conducted using ultraviolet light absorbance technology.

25. The method of claim 16 wherein spectrographic analysis of a compounded sample having an at least one unknown constituent at an unknown concentration is conducted using near-infrared energy absorbance technology and ultraviolet light absorbance technology.

26. The method of claim 16 further comprising the step of analyzing the sample having at least one unknown constituent at an unknown concentration for purity and sterility.

27. A method of determining the identity or concentration or both of at least one constituent in a sample having at least one unknown constituent or unknown concentration or both, for a requester, comprising the steps of:
accepting a request for determining and reporting to the requester the identity or concentration or or both of a sample having at least one unknown constituent or unknown concentration or both;
performing a spectrographic analysis of a sample having at least one predetermined constituent at at least one predetermined concentration, said spectrographic analysis performed by a technology selected from the group of technologies consisting of NIR energy absorbance technology, UV light absorbance technology and a combination of NIR energy absorbance technology and UV light absorbance technology;

obtaining energy absorbance curve data regarding the at least one predetermined constituent and the at least one predetermined concentration from the spectrographic analysis of the sample having at least one predetermined constituent at at least one predetermined concentration;

storing the obtained energy absorbance curve data from the analysis of the sample having at least one predetermined constituent at at least one predetermined concentration in a database of obtained energy absorbance curves obtained from spectrographic analysis of one or more samples having at least one predetermined constituent at at least one predetermined concentration;

receiving a sample having at least one unknown constituent or unknown concentration or both, said sample having no associated identifying indicia required for determining the identity or concentration or both of the at least one constituent;

performing a spectrographic analysis of the sample having at least one unknown constituent or unknown concentration or both, said spectrographic analysis performed by a technology selected from the group of technologies consisting of NIR energy absorbance technology, UV light absorbance technology and a combination of NIR energy absorbance technology and UV light absorbance technology;

obtaining energy absorbance curve data regarding the at least one unknown constituent or unknown concentration or both from the spectrographic analysis of the sample having at least one unknown constituent or unknown concentration or or both;

comparing the energy absorbance curve data obtained from the spectrographic analysis of the sample having at least one unknown constituent or unknown concentration or or both to the energy absorbance curve data obtained from the spectrographic analysis of the sample having at least one predetermined constituent at at least one predetermined concentration stored in the database;

identifying the at least one unknown constituent in the sample having at least one unknown constituent or unknown concentration or both or calculating a concentration of the at least one unknown constituent, or both, in the sample having at least one unknown constituent or unknown concentration or both from the energy absorbance curve data obtained from the spectrographic analysis of the sample having at least one unknown constituent or unknown concentration or both; and transmitting the identity of the at least one unknown constituent or the calculated concentration or both of the sample having at least one unknown constituent or unknown concentration or both to the requester through an electronic medium selected from the group of electronic media consisting of electronic mail, an interactive website, telephone transmission, facsimile transmission or any combination thereof.

28. The method of claim 27 further comprising electronic tracking of the steps of:

accepting a request for determining and reporting to the requester the concentration or both of a sample having at least one unknown constituent or unknown concentration or both;

performing a spectrographic analysis of a sample having at least one predetermined constituent at at least one predetermined concentration, said spectrographic analysis performed by a technology selected from the group of technologies consisting of NIR energy absorbance technology, UV light absorbance technology and a combination of NIR energy absorbance technology and UV light absorbance technology;

obtaining energy absorbance curve data regarding the at least one predetermined constituent and the at least one predetermined concentration from spectrographic analysis of the sample having at least one predetermined constituent at at least one predetermined concentration;

storing the obtained energy absorbance curve data from the analysis of the sample having at least one predetermined constituent at at least one predetermined concentration in a database of energy absorbance curves obtained from spectrographic analysis of one or more samples having at least one predetermined constituent at at least one predetermined concentration;

receiving a sample having at least one unknown constituent or unknown concentration or both, said sample having no associated identifying indicia required for determining the identity or concentration or both of the at least one constituent;

performing a spectrographic analysis of the sample having at least one unknown constituent or unknown concentration or both, said spectrographic analysis performed by a technology selected from the group of technologies consisting of NIR energy absorbance technology, UV light absorbance technology and a combination of NIR energy absorbance technology and UV light absorbance technology;

obtaining energy absorbance curve data regarding the at least one unknown constituent or unknown concentration or both from the spectrographic analysis of the sample having at least one unknown constituent or unknown concentration or both;

comparing the energy absorbance curve data obtained from the spectrographic analysis of the sample having at least one unknown constituent or unknown concentration or both to the energy absorbance curve data obtained from the spectrographic analysis of the sample having at least one predetermined constituent at at least one predetermined concentration stored in the database;

identifying the at least one unknown constituent in the sample having at least one unknown constituent or unknown concentration or both or calculating a concentration of the at least one unknown constituent, or both, in the sample having at least one unknown constituent or unknown concentration or both from the energy absorbance curve data obtained from the spectrographic analysis of the sample having at least one unknown constituent or unknown concentration or both; and transmitting the identity of the at least one unknown constituent or the calculated concentration or both of the sample having at least one unknown constituent or unknown concentration or both to the requester through an electronic medium selected from the group of electronic media consisting of electronic mail, an interactive website, telephone transmission, facsimile transmission or any combination thereof.

29. The method of claim 28 wherein the electronic tracking further comprises tracking through an interactive website.

30. A data processing system for managing a process for determining the identity or concentration or both of at least one constituent in a sample having at least one unknown constituent or unknown concentration or both, comprising:
- a computer processor for processing data; and
- computer software configured to perform data processing functions comprising;
  - a). determining spectrographical data regarding at least one constituent and concentration of a sample having at least one known constituent at a known concentration;
  - b). storing in a database the spectrographical data regarding at least one constituent and concentration of a sample having a at least one known concentration or purity;
  - c). determining spectrographical data regarding at least one constituent or a concentration or both of a sample having an unknown constituent or unknown concentration or both, said sample being devoid of any identifying indicia required to identify at least one constituent or determine concentration thereof;
  - d.) comparing the determined spectrographical data regarding the at least one constituent or concentration or both of the sample having at least one unknown constituent or unknown concentration or both to the spectrographical data in the database of spectrographical data regarding the at least one constituent and concentration of samples having at least one known constituent and known concentration;
  - e). applying an appropriate equation to calculate the concentration of the at least one constituent in the sample having at least one unknown constituent or unknown concentration or both or identifying said at least one constituent, or both, from the comparison of the spectrographical data in the database of spectrographical data regarding the at least one constituent and concentration of samples having at least one known constituent at a known concentration; and
  - f.) communicating the calculated concentration of the at least one constituent in the sample having at least one unknown constituent or unknown concentration or both.

31. The data processing system of claim 30 wherein the computer software configured to perform data processing functions includes the data processing function of processing a request for the determining spectrographical data of a sample having at least one unknown constituent or unknown concentration or both.

32. The data processing system of claim 30 wherein the data processing function of communicating the calculated concentration of the at least one constituent in a sample having at least one unknown constituent or unknown concentration or both further comprises communicating the calculated concentration by an electronic medium.

33. The data processing system of claim 32 wherein the electronic medium is electronic mail.

34. The data processing system of claim 32 wherein the electronic medium is an interactive website.

35. The data processing system of claim 30 wherein the computer software configured to perform data processing functions is configured to expand the database as a result of the performance of the steps of determining spectrographical data at least one known constituent at a known concentration of a sample having at least one known constituent at a known concentration and determining spectrographical data regarding at least one unknown constituent or unknown concentration or both of a sample having at least one unknown constituent or unknown concentration or or both.

* * * * *